United States Patent [19]

Lim et al.

[11] 4,017,497

[45] Apr. 12, 1977

[54] PROCESS FOR THE PREPARATION OF 14-HYDROXYMORPHINAN DERIVATIVES

[75] Inventors: Gary Lim, Candiac; John W. Hooper, Pierrefonds, both of Canada

[73] Assignee: Bristol-Myers Company, New York, N.Y.

[22] Filed: Nov. 18, 1975

[21] Appl. No.: 632,947

[52] U.S. Cl. .............................. 260/285; 260/340.5; 260/465 R
[51] Int. Cl.² ........................................ C07D 221/28
[58] Field of Search ..................................... 260/285

[56] References Cited

UNITED STATES PATENTS

| 3,166,559 | 1/1965 | Sawa et al. | 260/285 |
| 3,775,414 | 11/1973 | Monkovic et al. | 260/285 |
| 3,819,635 | 6/1974 | Pachter et al. | 260/285 |

FOREIGN PATENTS OR APPLICATIONS

| 40-12627 | 6/1965 | Japan |
| 1,028,407 | 5/1966 | United Kingdom |

OTHER PUBLICATIONS

Okabe, *J. Pharm. Soc.*, Japan (Yakugaku Zasshi), v.82, 1512–1514 (1962).
Lester et al., *Chemical Abstracts*, vol. 62, pp. 16311f–16313h, (1965).
Barltrop et al., *J. Chem. Soc.* 1038–1041 (1952).
Chemical Abstracts, vol. 47, 1165h (1953).
Sawa et al., *Tetrahedron*, v.24, 261–266 (1968).
Sawa et al., *Tetrahedron*, v.24, pp. 6185–6196 (1968).
Pettit et al., Desulfurization with Raney Nickel, Chap. 5, "Organic Reactions," v.12, N.Y. (1962), pp. 378–385.

*Primary Examiner*—Donald G. Daus
*Assistant Examiner*—Diana G. Rivers
*Attorney, Agent, or Firm*—Richard R. Lloyd

[57] ABSTRACT

N-substituted-14-hydroxy-3-substituted-morphinan derivatives have been found to possess potent narcotic agonist or antagonist activity. In particular, the compound 3,14-dihydroxy-N-cyclobutylmethylmorphinan has been found to possess potent agonist/antagonist activity. A new and novel total synthesis for the preparation of these compounds is described herein.

10 Claims, No Drawings

PROCESS FOR THE PREPARATION OF 14-HYDROXYMORPHINAN DERIVATIVES

BACKGROUND OF THE INVENTION

1. Field of the Invention

This invention embodies a new and novel process for the preparation of analgesics and/or narcotic antagonists.

2. Description of the Prior Art (A) (−)-14-hydroxy-3-methoxy-N-methylmorphinan and derivatives thereof have been described by Y. K. Sawa and H. Tada in Tetrahedron, 24, pp. 6185–6196. This paper reports the compound 14-hydroxy-3-methoxy-N-methylmorphinan as being prepared from 14-hydroxydehydrothebainone, as opium alkaloid.

(B) U.S. Pat. No. 3,166,599 disclosed compounds having the generic formula

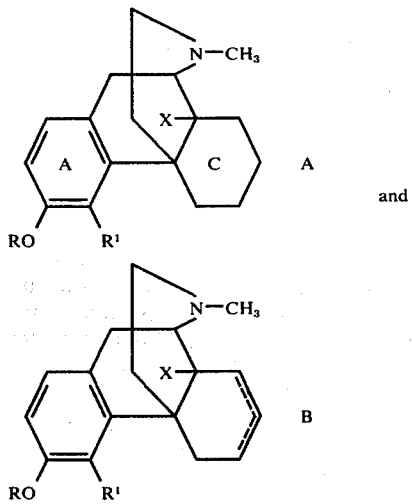

in which R represents a hydrogen atom or a (lower)alkyl group (e.g., methyl, ethyl, propyl), $R^1$ represents a hydrogen atom, an aryloxy group (e.g., phenyloxy, naphthyloxy) or a substituted phenyloxy, substituted naphthyloxy wherein the substituent is (lower)alkyl (e.g., methyl, ethyl, propyl), (lower)alkoxy, (e.g., methoxy, ethoxy, propoxy), nitro or amino, X represents a hydrogen atom or a hydroxyl group and, in Formula I, one or two double bond(s) exist(s) in the C ring.

(C) British Pat. No. 1,028,407 discloses compounds having the generic formula

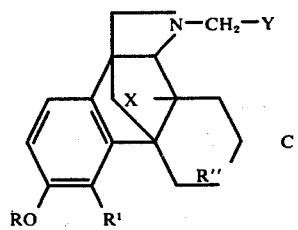

wherein R represents an alkyl group having not more than five carbon atoms (e.g., methyl, ethyl, propyl), $R^1$ represents a hydrogen atom or an aryloxy group (e.g., phenyloxy or naphthyloxy), R'' represents a methylene group, a carbonyl group or a ketalated carbonyl group (e.g., ethylenedioxymethylene or diethoxymethylene), X represents a hydrogen atom or hydroxyl group and Y represents an alkyl group having not more than five carbon atoms (e.g., methyl, ethyl or propyl), an aryl group (e.g., phenyl or naphthyl) or an aralkyl group in which the alkyl moiety has not more than five carbon atoms (e.g., benzyl or phenethyl) and shows various pharmacological activities such as analgesic activity, antitussive activity and anti-inflammatory activity.

(D) U.S. Pat. No. 3,819,635 discloses and claims the compounds having the formula

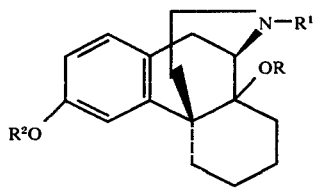

wherein $R^1$ is selected from the group comprising

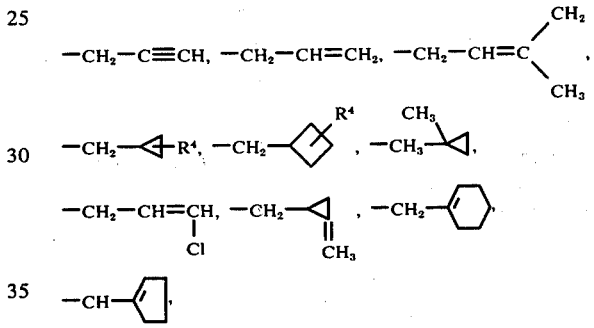

and (lower)alkenyl in which $R^4$ is H or $CH_3$, $R^2$ is selected from the group comprising H, (lower)alkyl,

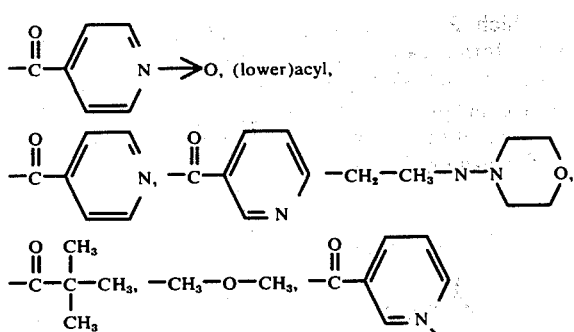

R is H, (lower)acyl, trichloroacetyl or cinnamoyl; or a pharmaceutically acceptable acid addition salt thereof and a process for their preparation which differs from that taught in reference E supra and that claimed in this invention.

(E) U.S. Pat. No. 3,775,414 discloses or claims a variation of the process found in U.S. Pat. No.

3,819,635 for the preparation of the same compounds prepared by this process. claim 1 reads as follows:

The process for the preparation of compounds having the formula

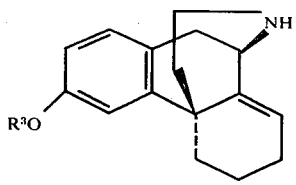

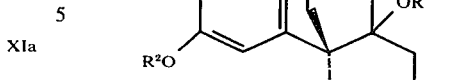

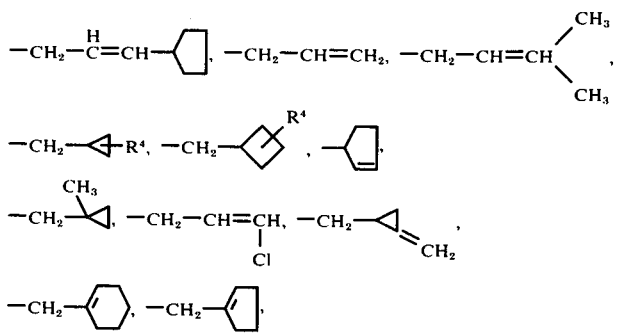

wherein $R^1$ is selected from the group comprising in which $R^3$ is (lower)alkyl, which process comprises the consecutive steps of (A) brominating the compound having the formula

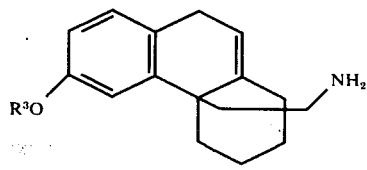  Va in which $R^3$ is (lower)alkyl, with liquid bromine in chloroform, carbon tetrachloride, benzene, toluene, xylene or methylene chloride in a ratio of about 1 mole of bromine per mole of compound Va, at about $-15°$ C. to about $+15°$ C., with stirring to produce the compound having the formula

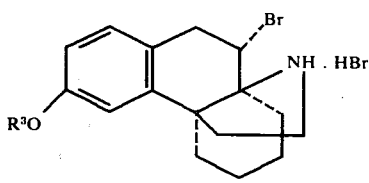  VIa in which $R^3$ is (lower)alkyl; and (B) heating Compound VIa in the presence of anhydrous sodium or potassium bicarbonate in dimethylformamide, benzene, dimethylacetamide, toluene, xylene, dioxane or tetrahydrofuran, in a ratio of no more than 1 mole of bicarbonate per mole of Compound VIa to produce Compound XIa.

SUMMARY OF THE INVENTION

This invention relates to the process for the preparation of compounds having the formula and (lower)alkenyl in which $R^4$ is H or $CH_3$, $R^2$ is selected from the group comprising H, (lower)alkyl, R is H, (lower)acyl, trichloroacetyl or cinnamoyl or a pharmaceutically acceptable acid addition salt thereof as prepared from 7-methoxy-$\beta$-tetralone.

DISCLOSURE OF THE INVENTION

This invention relates to the total synthesis of N-substituted-14-hydroxy-3-substituted morphinan derivatives having the formula

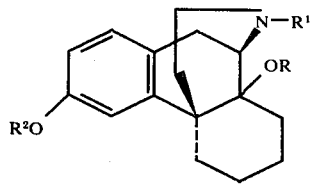  I wherein $R^1$ is selected from the group comprising

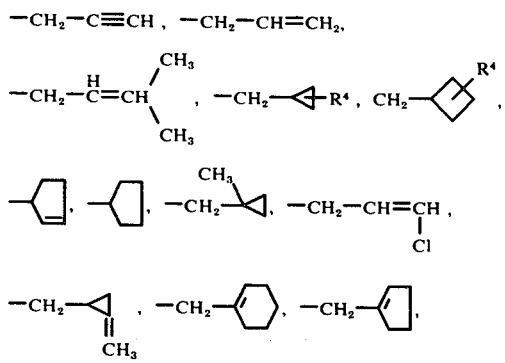

and (lower)alkenyl in which $R^4$ is H or $CH_3$, $R^2$ is selected from the group comprising H, (lower)alkyl,

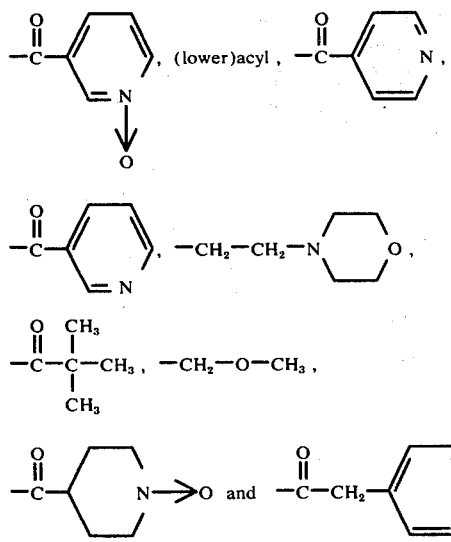

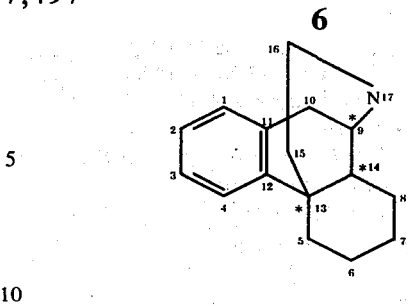

R is H, (lower)acyl, trichloroacetyl or cinnamoyl; or a pharmaceutically acceptable acid addition salt thereof.

Drug abuse by thrill-seeking youth or by people looking for an escape from the realities of everyday life has become more and more commonplace in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new non-addicting analgetics and/or narcotic antagonists.

It was an object of the present invention to develop a method of synthesis for the above-described Compounds I that would not be dependent upon opium alkaloids as starting materials and yet would be commercially feasible.

The objectives of the present invention have been achieved by the process of preparing the compounds of Formula I by their total synthesis from the readily available starting material 7-methoxy-β-tetranone.

The compounds of the instant invention have the basic morphinan nucleus which is numbered and represented by the following plane formula:

Although there are three asymetric carbons (asterisks) in the morphinan molecule, only two diastereoisomeric (racemic) forms are possible because the iminoethano system, attached to position 9 and 13, is geometrically constrained to a cis-(1,3-diaxial)-fusion. These racemates can therefore differ only at the junction of rings B and C—in other words, in the configuration of carbon 14. The only variable will be the cis and trans relationship between the 5 (13) and 8 (14) bonds (Analgetics, Ed. George de Stevens, Academic Press, New York, p. 137 (1965)).

When in the compounds of the present invention, the 5 (13) and 8 (14) bonds are trans to each other, we have compounds commonly designated as "isomorphinans." On the other hand, when 5 (13) and 8 (14) are cis to each other, we have compounds commonly designated as "morphinans." The use of a graphic representation of a "morphinans." The use of a graphic representation of a "morphinan" or "isomorphinan" is meant to include the dl racemic mixture and the resolved d and l isomers thereof.

The isomorphinans disclosed and claimed herein are primarily useful as intermediates in the preparation of the biologically potent analgetic and/or narcotic antagonist agent of the present invention.

In addition, the isomorphinan and morphinan compounds of the present invention can each exist as two optical isomers, the levorotatory and dextrorotatory isomers. The optical isomers can be graphically illustrated as:

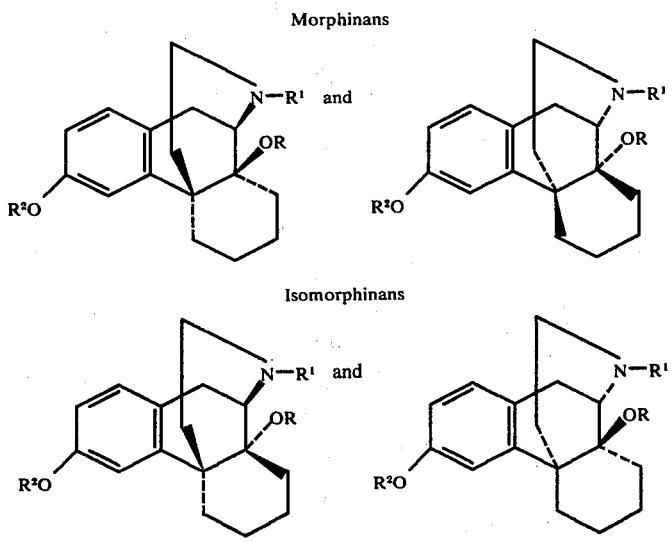

The present invention embodies all of the isomorphinan and morphinan isomers including the optical isomers in their resolved form.

The optical isomers can be separated and isolated by fractional crystallization of the diastereoisomeric salts formed, for instance, with d- or l-tataric acid or D-(+)-α-bromocamphor sulfonic acid. The levorotatory isomers of the compounds of the present invention are the most referred embodiments.

For the purpose of this disclosure and the appended claims, the term (lower)alkyl is defined as an alkyl radical containing 1 to 6 carbon atoms. (Lower)alkenyl is defined as a hydrocarbon radical of 3 to 7 carbons containing one double bond. The term (lower)acyl is an acyl radical of 2 to 6 carbon atoms, e.g., acetyl, propionyl, isobutyryl, etc. The term pharmaceutically acceptable acid addition salt is defined to include all those inorganic and organic acid salts of the compounds of the instant invention, which salts are commonly used to produce nontoxic salts of medicinal agents containing amine functions. Illustrative examples would be those salts formed by mixing the compounds of Formula I with hydrochloric, sulfuric, nitric, phosphoric, phosphorous, hydrobromic, maleic, malic, ascorbic, citric or tartaric, pamoic, lauric, stearic, palmitic, oleic, myristic, lauryl sulfuric, naphthalenesulfonic, linoleic or linolenic acid, and the like.

The compounds of the instant invention are prepared by a total synthesis comprising at least 9 steps. Surprisingly, the synthesis is efficient and appears commercially feasible. The process is outlined in Charts I, II and III.

Reaction Scheme I

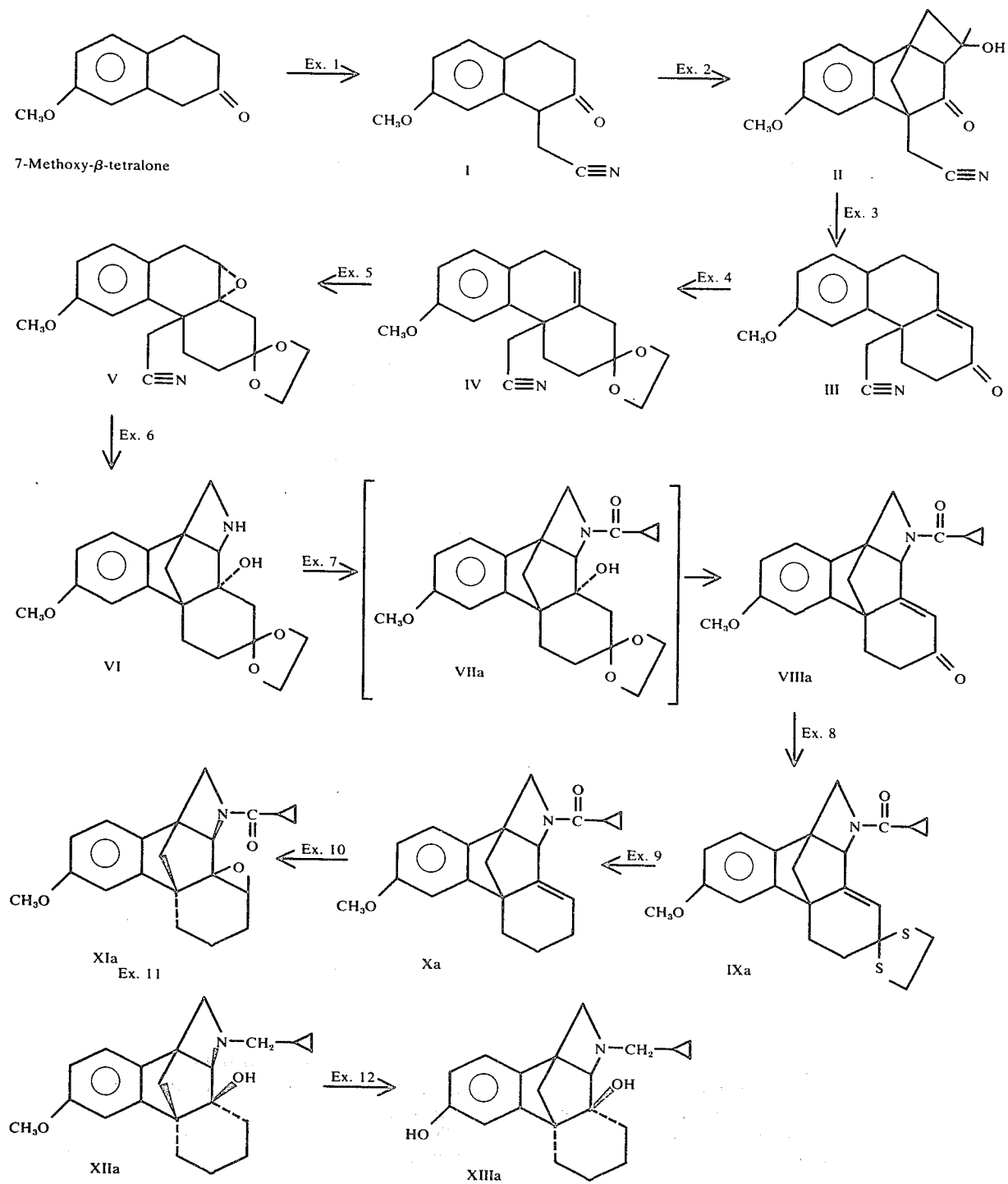

4,017,497
Chart II
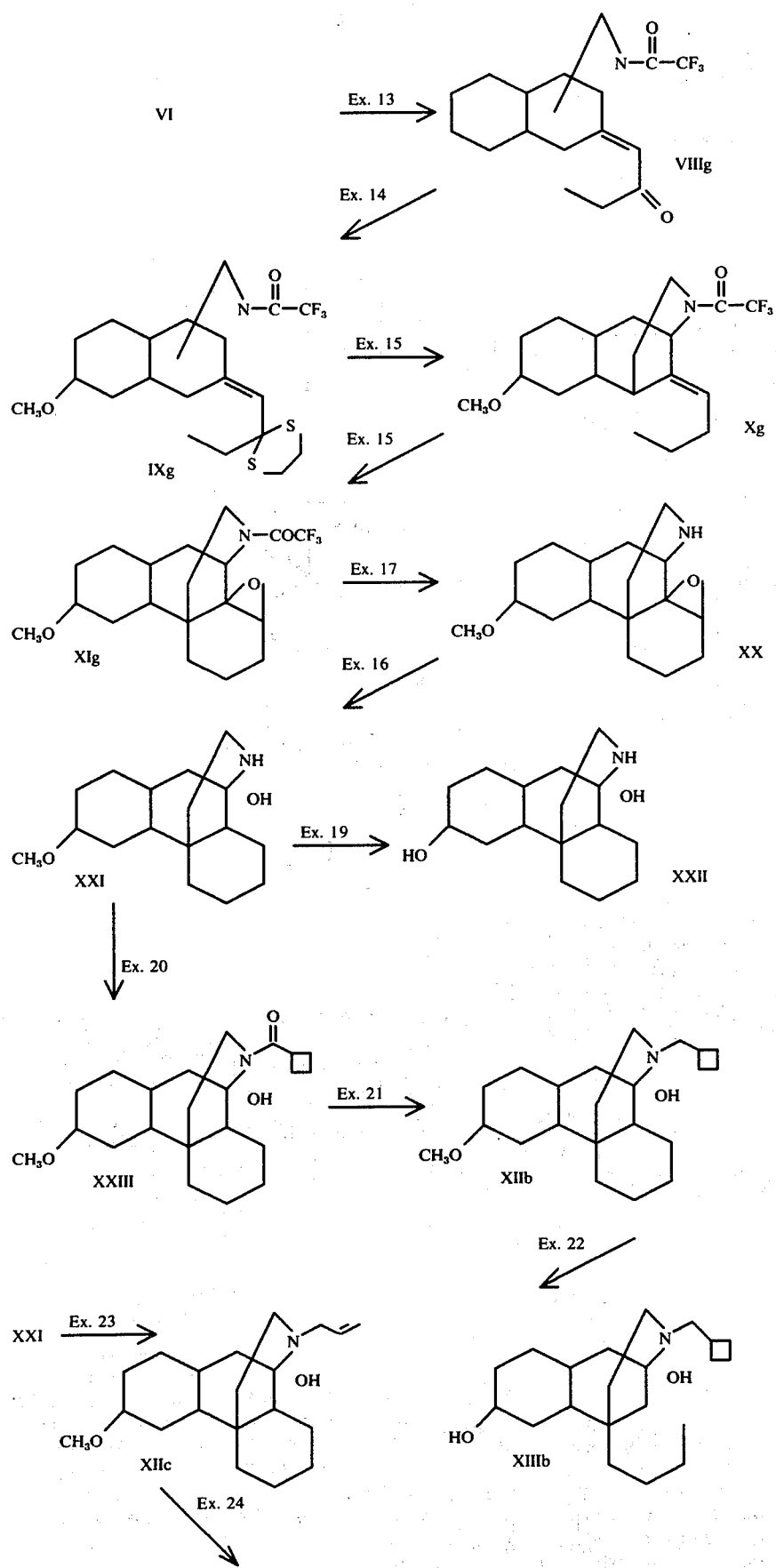

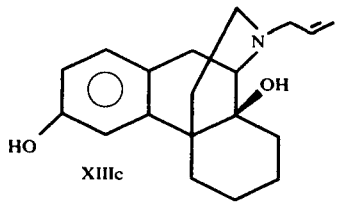

Chart III

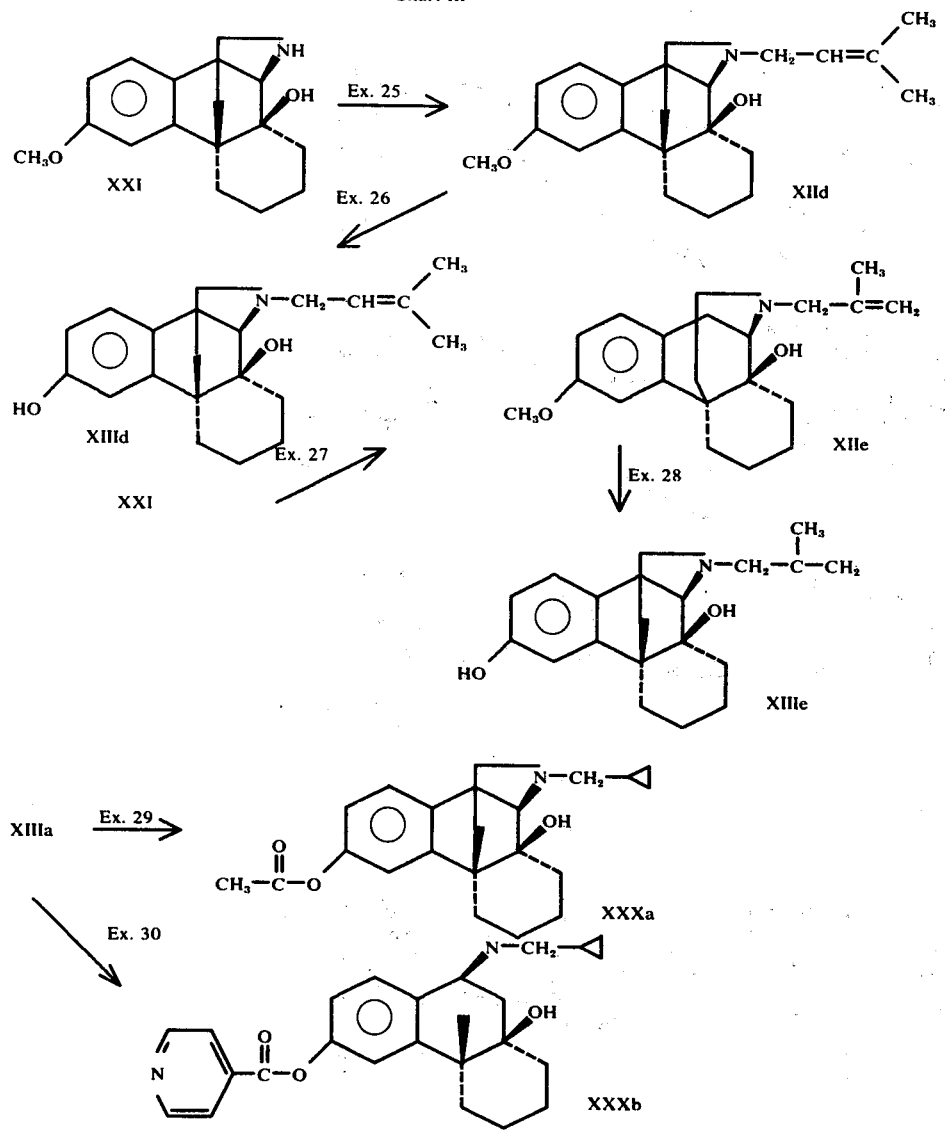

For the purpose of this disclosure the term inert organic solvent means an organic solvent that does not participate in the reaction to the extent that it emerges unchanged from the reaction. Such solvents are methylene chloride, chloroform, dichloroethane, tetrachloromethane, benzene, toluene, ether, ethyl acetate, xylene, tetrahydrofuran, dioxane, dimethylacetamide, and the like when an acid halide is employed. When an alkylation reaction is being performed, the inert solvent used may also include (lower)alkanols such as methanol, ethanol, n-propanol, isopropanol and the like. The term organic tertiary amine means a tertiary amine commonly employed as a proton acceptor in alkylation and acylation reactions. Such amines are tri(lower)alkylamines, e.g., trimethylamine, triethylamine, and the like, pyridine, dimethylaniline, N-methylpiperidine, and the like.

A preferred embodiment of the present invention is the process of preparing the compound having the formula

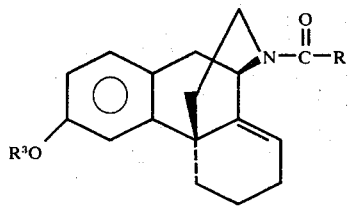

in which R³ is (lower)alkyl and R is selected from the group consisting of

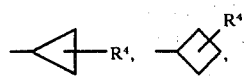

—CF₃ and —O—R¹ in which R¹ is (lower)alkyl and R⁴ is H or CH₃; which process comprises treating the compound having the formula

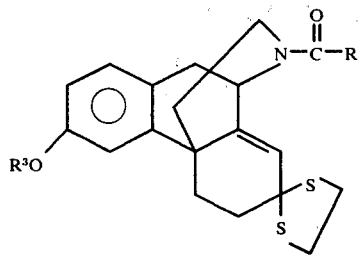

in which R is as defined above with Raney nickel in a (lower)alkanol to produce compound X.

A more preferred embodiment is the process of preparing the compound X in which R³ is (lower)alkyl and R is selected from the group consisting of

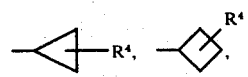

—CF₃ and OR¹ in which R¹ is (lower)alkyl and R⁴ is H or CH₃; which process comprises the consecutive steps of (A) treating the compound having the formula

VI

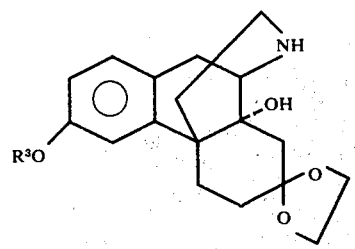

in which R³ is (lower)alkyl with an acylating agent having the formula

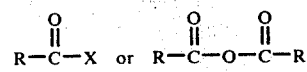

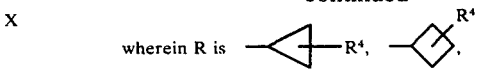

CF₃, or —OR¹ in which R¹ is (lower)alkyl, R⁴ is H or CH₃, and X is chloro, bromo, iodo or a mixed anhydride moiety, or its functional equivalent in a molar ratio of about 1 to 2.0 moles of acylating agent per mole of compound VI, in the presence of a tertiary amine to produce the compound having the formula

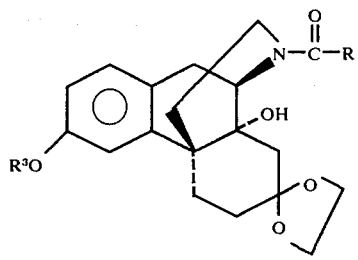

in which R³ and R are as above;

(B) heating compound VII with sulfuric acid in a (lower)alkanol to produce the compound having the formula

VIII

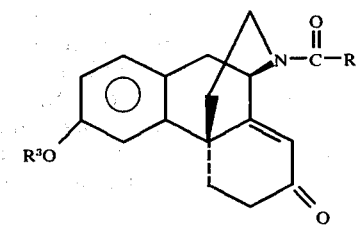

in which R³ and R are as above;

(C) treating compound VIII with excess ethanedithiol and boron trifluoride etherate in acetic acid to produce the compound having the formula

IX

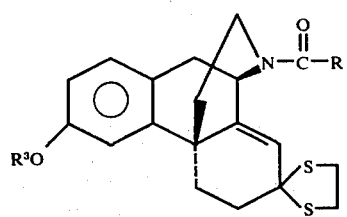

in which R³ and R are as above; and (D) heating compound IX with Raney nickel in a (lower)alkanol to produce compound X.

A more preferred embodiment is the process of preparing the compound X in which R³ is (lower)alkyl and R selected from the group consisting of

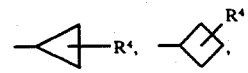

—CF₃ and OR¹ in which R¹ is (lower)alkyl and R⁴ is H or CH₃; which process comprises the consecutive steps of (A) treating the compound having the formula

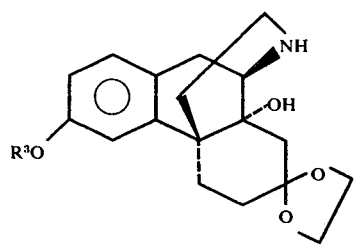

VI in which R³ is (lower)alkyl with an acylating agent having the formula

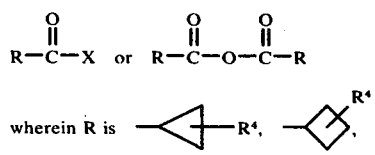

wherein R is 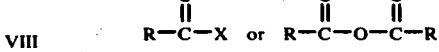

CF₃, or —OR¹ in which R¹ is (lower)alkyl, R⁴ is H or CH₃ and X is chloro, bromo or iodo, in a ratio of about 1 to 1.3 moles of acylating agent per mole of compound VI, in an inert organic solvent selected from the group consisting of benzene, toluene, xylene, methylene chloride, chloroform, ether, dioxane, tetrahydrofuran, in the presence of a tertiary amine selected from the group consisting of trimethylamine, triethylamine, pyridine, dimethylaniline, N-methylpyrrolidine, N,N-dimethylpiperazine and N-methylpiperidine in a molar ratio of 1 to 2 parts tertiary amine per mole of acylating agent to produce the compound having the formula

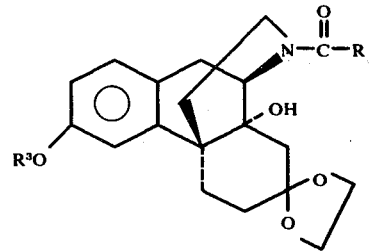

VII in which R³ and R are as defined above;

(B) heating compound VII with 0.3 to 0.7N sulfuric acid in a (lower)alkanol until dehydration occurs to produce the compound having the formula

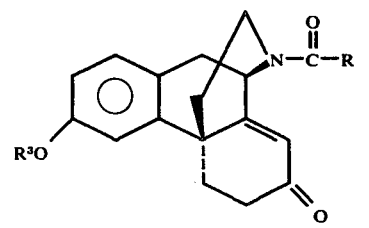

VIII in which R³ and R are as above;

(C) treating compound VIII with excess ethanedithiol and boron trifluoride etherate in acetic acid at room temperature for at least 3 hours to produce the compound having the formula

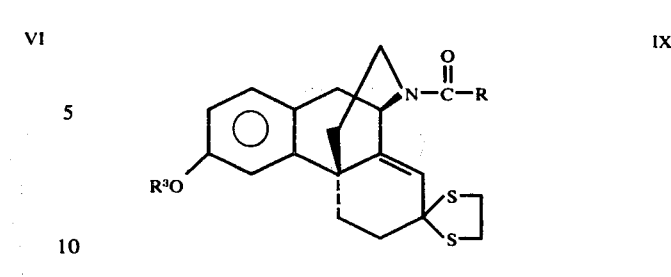

IX in which R³ and R are as above; and (D) heating compound IX with Raney nickel in a (lower)alkanol to produce compound X.

The most preferred embodiment in the process for the preparation of the compound having the formula

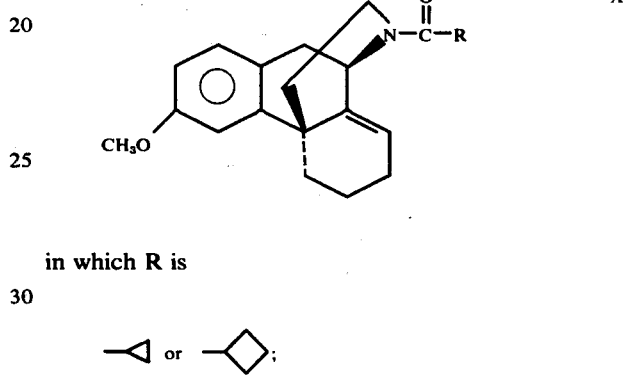

X in which R is

which process comprises the consecutive steps of
(A) treating the compound having the formula

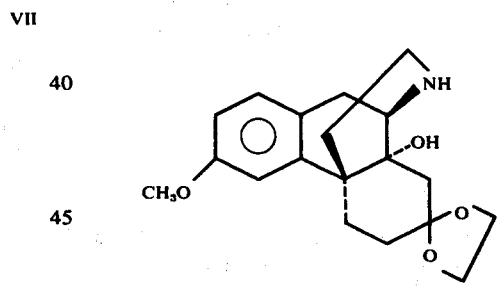

with an acylating agent having the formula

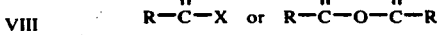

in which R is

and X is chloro, bromo, or iodo, in a ratio of about 1 to 1.2 moles of acylating agent per mole of compound VI, in methylene chloride, in the presence of pyridine in a ratio of 1 to 2 moles of pyridine per mole of acylating agent, in a temperature range of about −10° C to +40° C to produce the compound having the formula

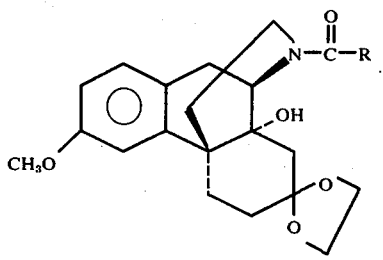
VII in which R is

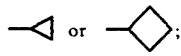

(B) heating compound VII with about 0.5 N sulfuric acid in methanol for about two to four hours to produce the compound having the formula

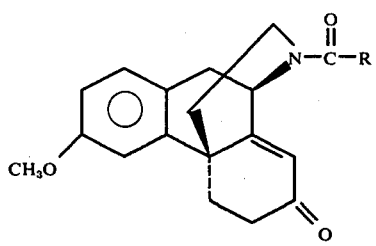
VIII in which R is

(C) treating compound VIII with excess ethanediol and boron trifluoride etherate in acetic acid at room temperature for at least 3 hours to produce the compound having the formula

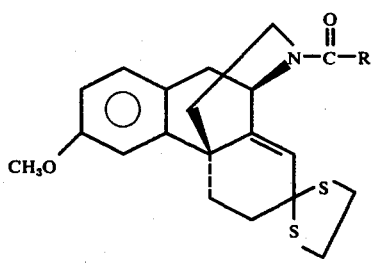
IX in which R is

and (D) refluxing compound IX with Raney nickel in ethanol for about two hours to produce compound X.

A preferred embodiment of the present invention is the compound having the formula

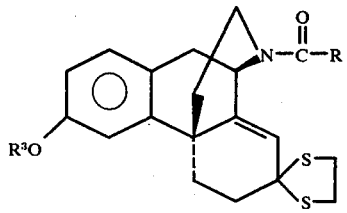
IX in which R is

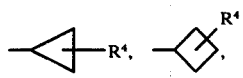

$CF_3$ or $-OR^1$ in which $R^1$ is (lower)alkyl, $R^4$ is H or $CH_3$ and $R^3$ is lower alkyl.

A more preferred embodiment is the compound IX in which $R^3$ is $CH_3$ and $R^4$ is H.

A preferred embodiment is the compound having the formula

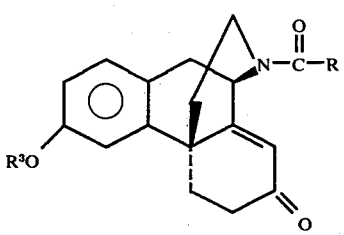
VIII in which $R^3$ is (lower)alkyl and R is

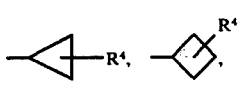

$CF_3$ or $O-R^1$ in which $R^1$ is (lower)alkyl and $R^4$ is H or $CH_3$.

The compound VIII in which $R^3$ is $CH_3$ and $R^4$ is H.

EXAMPLE 1

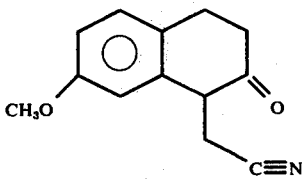

7-Methoxy-2-oxo-1,2,3,4-tetrahydro-1-naphthalene acetonitrile (1)

A mixture of 7-methoxy-2-tetralone (472 g., 2.68 mole), pyrrolidine (241 g., 3.40 mole) and benzene (2.5l) was refluxed under nitrogen with water separation (Dean-Stark trap) for 2 hrs. and then distilled for a further 1 hr. (1.2l) of distillate). Chloroacetonitrile (324 g., 4.30 mole) was added during 15 mins. and the mixture was refluxed for 4 hrs. and then left at room temperature overnight. Water (1.5l) was added and the mixture was refluxed for 3 hrs. The organic layer was separated while still hot, washed with 3N sulphuric acid (500 ml.) and filtered with suction through a pad of magnesium sulphate. The product crystallized from benzene and from benzene-ether (two crops) as yellow prisms (484 g., 84%); m.p. 97°–99° C.

I.R. (infrared) γmax 1720 (CO), 2250 (CN) cm⁻¹. N.M.R. (Nuclear Magnetic resonance); τ 2.67 (d, J = 6 Hz, 1H, C-5H); 2.9 – 3.15 (m, 2H, C-6 and C-8 H); 6.17 (s, 4H, OCH₃ and C 1H); 6.98 (s, 2H, —CH₂C ≡ N); Anal. calc'd. for $C_{13}H_{13}NO_2$: C, 72.54; H, 6.08; N, 6.51. Found: C, 72.59; H, 6.14; N, 6.41.

EXAMPLE 2

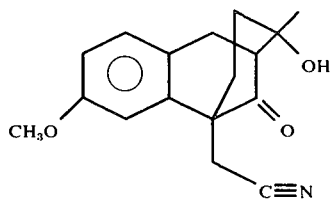

5,6,7,8,9,10-Hexahydro-8-hydroxy-3-methoxy-8-methyl-11-oxo-5,9-methanobenzocyclooctene-5-acetonitrile (II).

A 25% solution of sodium methoxide in methanol (30 ml) was added under nitrogen to a suspension of the finely divided ketonitrile I (215.1 g., 1.00 mole) in methanol (2) at −10° C. This was stirred vigorously while methyl vinyl ketone (95 g., 136 mole) freshly distilled) in methanol (375 ml) was added dropwise at −3° to −6° C during 6 hrs. The mixture was stirred at 0° C. for further 1 hr. and then the product was filtered off and washed with cold methanol to give colorless prisms of the ketol (261 g., 91.5%); m.p. 206°–208° C.

I.R. γmax 1715 (CO), 2250 (CN), 3450 (OH) cm⁻¹. N.M.R. τ (DMSO) 2.81 (d, J = 9 Hz, 1H, C - 1H); 2.95 – 3.20 (m, 2H, C-2 and C-4H); 4.90 (s, 1H, OH); 6.22 (s, 3H, OCH₃), 8.88 (s, 3H, C-8 Me). Anal. calc'd. for $C_{17}H_{19}NO_3$: C, 71.57; H, 6.72; N, 4.91. Found: C, 71.41; H, 6.49; N, 4.90.

EXAMPLE 3

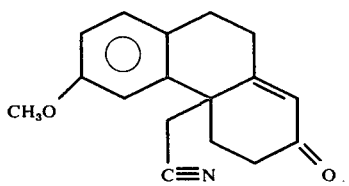

6-Methoxy-2,3,4,4a,9,10-hexahydro-2-oxo-phenanthrene-4a-acetonitrile (III)

A mixture of the ketol II (285 g., 1.00 mole), pyrrolidine (213 g., 3.0 mole), acetic acid (180 g., 3.0 mole) and benzene (2l) was refluxed with water separation (Dean-Stark trap) under nitrogen for 30 hours. A buffer solution of sodium acetate (285 g) in water (670 ml) and acetic acid (560 ml) was added and refluxing was continued for 24 hours. The mixture was cooled, washed with 3N sulphuric acid (2 × 500 ml) and work up to give the crude enone III (orange gum). A sample crystallized from methanol as pale yellow prisms; m.p. 133°–134° C.

I.R. γmax 1670 (CO), 2250 (CN) cm⁻¹. N.M.R. τ 4.02 (s, 1H, olefinic H); 6.20 (s, 3H, OCH₃); 7.03 (s, 2H, CH₂CN). Anal. calc'd. for $C_{17}H_{17}NO_2$: C, 76.38; H, 6.41; N, 5.24. Found: C, 76.55; H, 6.46; N, 5.19.

EXAMPLE 4

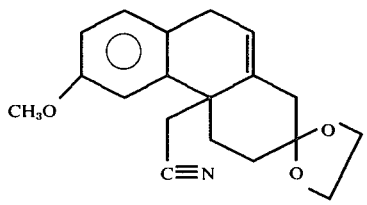

2,2-Ethylenedioxy-1,2,3,4,4a,9-hexahydro-6-methoxy-4a-phenanthrene acetonitrile (IV).

A mixture of the crude enone III, benzene (2.5 l), ethylene glycol (150 ml) and p-toluenesulphonic acid (4.0 g) was refluxed with water separation (Dean-Stark trap) for 17 hrs. cooled and evaporatd at reduced pressure to approximately 500 ml. Dichloromethane (2.5 l) was added; the mixture worked up, the organic solution was evaporated to approximately 700 ml and diluted with ether (1.5l). The ketal IV was obtained in two crops as colorless needles (249 g, 80%); m.p. 174°–175° C.

I.R. γmax 2245 (CN) m⁻¹. N.M.R. τ 2.95 (d, J = 9Hz, 1H, C-1H); 3.1 – 3.4 (m, 2H, C-2 and C-4H); 4.03 – 4.25 (m, 1H, olefinic H); 6.05 (s, 4H, ketal H's); 6.22 (s, 3H, OCH₃); 6.4 – 6.8 (m, 2H, ArCH₂—). Anal. calc'd. for $C_{19}H_{21}NO_3$: C, 73.28; H, 6.80; N, 4.50. Found: C, 73.32; H, 6.83; N, 4.47.

EXAMPLE 5

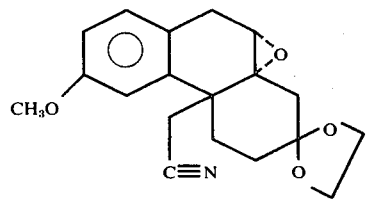

10α,10aα-Epoxy-2,2-ethylenedioxy-6-methoxy-1,2,3,4,4a,9,10,10a-octahydrophenanthrene-4aβ-acetonitrile (V)

A solution of the ketal IV (398.4 g., 1.26 mole) in dichloromethane (3.5l) was cooled in an ice bath and stirred while m-chloroperoxybenzoic acid (85%, 340 g., 1.67 mole) was added portionwise during 25 mins. The ice bath was removed and the mixture was stirred at room temperature for 18 hrs. The suspension was washed with 5% sodium sulphite solution, then with 10% sodium bicarbonate solution (X2), dired over anhydrous sodium sulphate and evaporated to approximately 1l. Filtration afforded colorless needles of the α-epoxide (270.5 g., 64.5%) m.p. 205°–206° (the β epoxide is in the mother liquor).

I.R. γmax 2250 (CN) cm⁻¹. N.M.R. τ 2.85 – 3.85 (m, 3H, ArH); 5.80 – 6.05 (m, 4H, ketal H's); 6.23 (s, 3H, OCH₃); 6.55 – 6.80 (m, 3H); 7.26 (s, 2H, CH₂CN). Anal. calc'd. for C H NO: C, 69.71; H, 6.47; N, 4.22.

EXAMPLE 6

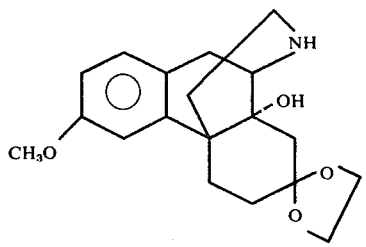

7,7-Ethylenedioxy-14-hydroxy-3-methoxyisomorphinan (VI)

A mixture of the finely divided epoxide V (60 g) and Raney nickel (120 g) in methanol (4l) containing dissolved ammonia (50 g) was stirred vigorously in an atmosphere of hydrogen for 24 hrs. The methanol was decanted and the nickel was washed with methanol (3 × 400 ml). The combined methanol solution was filtered through celite (diatomaceous earth) and evaporated to a green gum. This was partitioned between dichloromethane and dilute aqueous ammonia and worked up to give a gum which was digested with refluxing ether (600 ml) until it had all dissolved and a fine white suspension had formed. This was filtered to give the isomorphinan VI as colorless crystals (40.0 g., 66%); m.p. 232°–234° C.

I.R. γmax 3275 (NH), 3400 (OH) cm⁻¹. N.M.R. τ 3.12 (d, J = 8 Hz, 1H, C-1H); 3.33 – 3.60 (m, 2H, C-2 and C-H H's); 5.83 (s, 1H, OH); 6.10 (s, 4H, ketal H's); 6.32 (s, 3H, OCH₃). Anal. calc'd. for C₁₉H₂₅NO₄: C, 68.86; H, 7.60; N, 4.23. Found: C, 68.75; H, 7.75; N, 4.06.

EXAMPLE 7

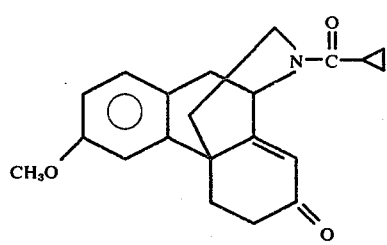

N-Cyclopropanecarbonyl-3-methoxy-7-oxo-Δ⁸,¹⁴-morphinan VIIIa

A suspension of the isomorphinan VI (3.31 g, 10 mmole) in methylene chloride 120 ml) containing pyridine (1.6 g, 20 mmole) was stirred and cooled in an ice bath while a solution of cyclopropanecarboxylic acid chloride (1.75 g, 12 mmole) in methylene chloride 20 ml) was added dropwise during 15 mins. After 1½ hr., the mixture was washed with water and concentrated to an oil VII. This oil was picked up in methanol (100 ml) and 1.5 N sulfuric acid (50 ml) then heated to reflux for 3½ hrs. The mixture was concentrated by slow distillation until crystallization occurred (50 ml distillate) then allowed to cool. The product VIII was collected and a sample crystallized from ether to give colorless prisms; m.p. 108°–109° C.

I.R. γmax 1630 (NCOR), 1680 (CO) cm⁻¹. N.M.R. τ 2.75 – 3.25 (m, 3H, ArH); 3.93 (s, 1H olefinic H); 4.20 –4.80 (m, 1H, C-9H); 6.17 (s, 3H, OCH₃); 8.70 – 9.35 (m, 5H, cyclopropyl H's). Anal. calc'd. for C₂₁H₂₂NO₃: C, 74,75; H, 6.87; N, 4.15. Found: C, 74.52; H, 6.87; N, 4.11.

EXAMPLE 8

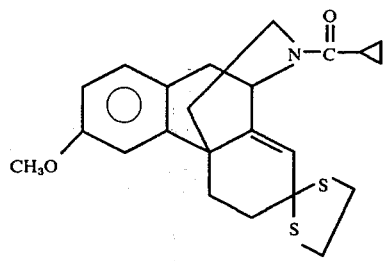

N-Cyclopropanecarbonyl-7,7 ethylene dithio-3-methoxy-Δ⁸,¹⁴-morphinan (IXa)

A solution of the above crude enone VIIIa in acetic acid (30 ml.) and ethanedithiol (4.5 ml) was treated with boron trifluoride etherate (0.5 ml) and allowed to stand at room temperature overnight. The mixture was partitioned between benzene and water. The benzene layer was concentrated to give crude thioketal IX as a colorless foam (3.86 g, 96%). A sample was crystallized from ethanol; m.p. 182°–184° C (decomp.).

I.R. γmax 1610 (CONR) cm⁻¹. N.M.R. τ 2.95 – 3.5 (m, 3H, ArH); 4.15 (s, 1H, olefinin H); 4.60 – 5.25 (m, 1H, C-9H); 6.26 (s, 3H, OCH₃); 6.73 (s, thioketal H's); 8.85 – 9.45 (m, 5H, cyclopropyl H's). Anal. calc'd. for C₂₃H₂₇NO₂S₂: C, 66.79; H, 6.58; N, 3.39; S, 15.51. Found: C, 66.88; H, 6.83; N, 3.37; S, 15.64.

EXAMPLE 9

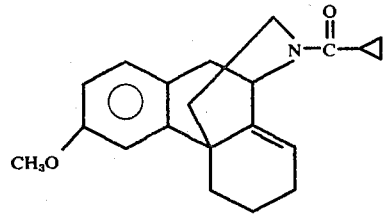

N-Cyclopropylcarbonyl-3-methoxyΔ⁸,¹⁴-morphinan (Xa)

A mixture of the crude thioketal IXa, Raney nickel (deactivated by refluxing for 15 mins. in ethanol, 42 g) and ethanol (250 ml) was refluxed for 2 hrs. The mixture was filtered through celite and the nickel washed well with hot ethanol. The ethanol solution was concentrated and the crude product V obtained was recrystallized from ether (overall yield from VI was 65%); m.p. and mixed with authentic product was 133°–135° C. The I.R. and N.M.R. spectra were identical with those of an authentic specimen.

EXAMPLE 10

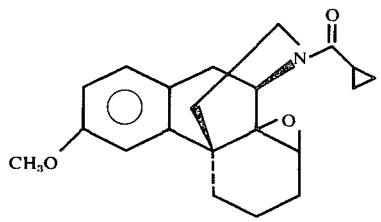

N-cyclopropylcarbonyl-8,14-epoxy-3-methoxymorphinan (XIa)

To a solution of 3.33 g. (10.3 mmole) of XVI in 35 ml. $CH_2Cl_2$ at 0° C. was added 2.31 g. of 85% m-chloroperbenzoic acid (11.3 mmole). The mixture was stirred at 0°–5° C. until all the peracid was dissolved. The mixture was left at room temperature for 6 hours. Work up in usual manner afforded an oil which was dissolved in 10 ml. of ether and left for 24 hours at 5° C. The solid was filtered off to yield 2.3 g. (66%); M.P. 134°–36° c.

Recrystallization from a $CH_2Cl_2$-ether mixture afforded a sample melting at 140°–42° C. The IR and NMR spectra were consistent with the structure.

Anal. Calc'd. for $C_{21}H_{25}NO_3$ (percent): C, 74.31; H, 7.42; N, 4.13. Found (percent): C, 74.13; H, 7.39; N, 4.13.

EXAMPLE 11

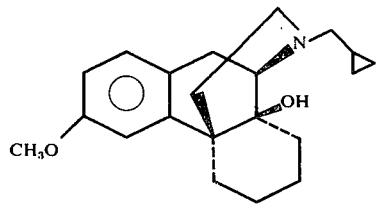

N-cyclopropylmethyl-14-hydroxy-3-methoxymorphinan (XIIa)

To stirred suspension of 1.8 g. of $LiAlH_4$ in 50 ml. of anhydrous THF was added dropwise during 5 minutes a solution of 6.0 g. (17 mmole) of XVII in 10 ml. THF. The mixture was refluxed during one hour and then worked up in the usual manner. The product was dissolved in petroleum ether (B.P. 40°–60° C.) and filtered through celite-charcoal to give 5.73 g. of an oil. Treatment with anhydrous HCl in ether afforded 6.15 g. (95.5%) of the hydrochloride salt, M.P. 223°–25° C. Recrystallization from methanol-ether increased the M.P. to 259°–60° C. The IR and NMR spectra were consistent with the structure.

Anal. Calc'd. for $C_{21}H_{29}NO_2 \cdot HCl \cdot \frac{1}{2}H_2O$ (percent): C, 67.67; H, 8.37; N, 3.76. Found (percent): C, 67.70; H, 8.02; N, 3.72.

EXAMPLE 12

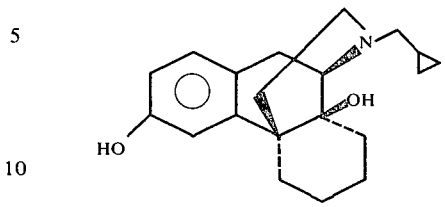

3,14-dihydroxy-N-cyclopropylmethylmorphinan (XIIIa)

METHOD A

A mixture of 4.1 g. (11.7 mmole) of the hydrochloride salt of XVIII and 13.4 g. of anhydrous pyridine hydrochloride was heated under nitrogen at 187°–95° C. for 1 hour. The cooled mixture was dissolved in 40 ml. of water, basified with aqueous ammonia and extracted with 2 × 40 ml. of ether. Drying and evaporation of the solvent yield 3.0 g. of semi-solid product, which was dissolved in ether. After treatment with charcoal, the product crystallized to yield 2.54 g. (69.4%) of free base M.P. 157°–59° C. The hydrochloride salt, recrystallized from methanolacetone, had a M.P. 170°–81° C. with contraction starting at 163. The product analyzed for ½ molecule of methanol of crystallization. The IR and NMR spectra were consistent with the structure.

Anal. calc'd. for $C_{20}H_{27}NO_2 \cdot HCl \cdot \frac{1}{2}CH_3OH$ (percent): C, 67.32; H, 8.37; N, 3.83. Found (percent): C, 67.56; H, 8.20; N, 3.90.

METHOD B

Into a cooled (Dry Ice-acetone) three-l. three-necked flask equipped with a mechanical stirrer, dropping funnel and a gas trap was placed a solution of 133.1 g. (0.5312 mole) of $BBr_3$ in 250 ml. of dry methylene chloride. Then a solution of 58 g. (0.177 mole) of the free base XVIII in 1.2 l. of dry methylene chloride was added dropwise under nitrogen (time=1 hour).

After the addition had been completed, the reaction mixture was stirred in the cold for one hour, and then at room temperature for three hours. (1) The reaction mixture was cooled (ice-bath) and carefully decomposed with 350 ml. of cold water. (2) It was transferred into a four l. Erlenmeyer flask and treated carefully with 200 ml. of concentrated ammonium hydroxide with cooling and stirring. The layers were separated and the aqueous layer extracted with 200 ml. of methylene chloride. The combined organic extracts were dried ($MgSO_4$) and evaporated, in vacuo, to give an oil in quantitative yield.

The oil was taken up in 250 ml. of reagent acetone, cooled, and treated with 17 ml., of concentrated hydrochloride acid. After standing in the cold for 18 hrs., the solid was collected by filtration and washed with 2 × 60 ml. of cold acetone. The product was recrystallized from 90% ethyl alcohol. The IR and NMR spectra were consistent with the structure. Yield: 55.0 g. (86.3%); M.P. 275°–77° C. (dec.).

Anal. calc'd. for $C_{20}H_{27}NO_2 \cdot HCl$ (percent): C, 68.65; H, 8.07; N, 4.00. Found (percent): C, 68.01; H, 8.17; N, 3.88.

(1) During one hour at −70° C., the boron complex hardened and stirring was very difficult. The cold bath

EXAMPLE 13

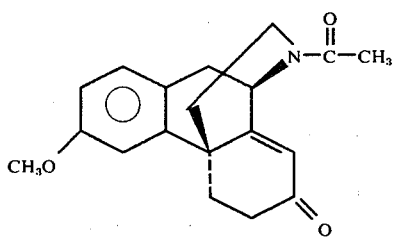

VIIIg

3-Methoxy-N-trifluoroacetyl-7-oxo-Δ$^{8,14}$-morphinan (VIIIg)

Substitution in the procedure of example 7 for the cyclopropanecarboxylic acid chloride used therein of an equimolar quantity of trifluoroacetal chloride produces the title product.

EXAMPLE 14

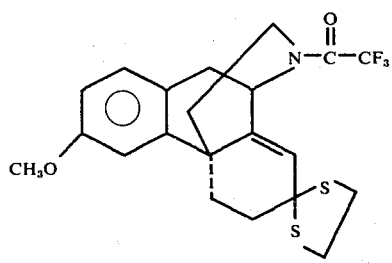

IXg

3-Methoxy-N-trifluoroacetyl-7,7-ethylenedithio-Δ$^{8,14}$-morphinan (IXg)

Substitution in the procedure of example 8 for the N-cyclopropanecarbonyl-3-methoxy-7-oxo-Δ$^{8,14}$-morphinan used therein of an equimolar quantity of 3-methoxy-N-trifluoroacetyl-7-oxo-Δ$^{8,14}$-morphinan (VIIIg) used therein produces the title compound IXg.

EXAMPLE 15

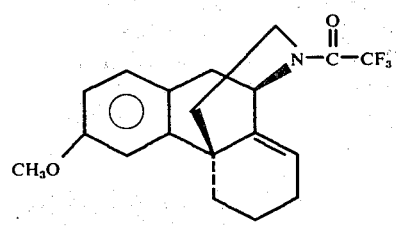

Xg

3-Methoxy-N-trifluoroacetyl-Δ$^{8,14}$-morphinan (Xg)

Substitution in the procedure of example 9 for the N-cyclopropanecarbonyl-7,7-ethylenedithio-3-methoxy-Δ$^{8,14}$-morphinan used therein of an equimolar quantity of 3-methoxy-N-trifluoro-7,7-ethylenedithio-Δ$^{8,14}$-morphinan (IXg) produces the title compound.

EXAMPLE 16

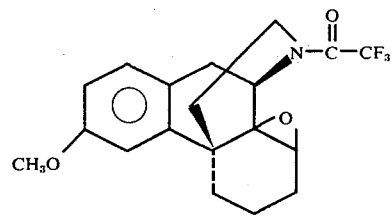

8,14-epoxy-3-methoxy-N-trifluoroacetylmorphinan (XIg)

The procedure is the same as that described for the preparation of Compound VII in Example 6 using the following materials: 3.85 (10.96 mmole) of Compound XX; 2.07 g. (12 mmole) of 85% m-chloroperbenzoic acid; and 30 ml. of methylene chloride. Reaction time: 6 hours.

After the usual work up, the residual oil was covered with 5 ml. of ether. Crystals formed which were collected by filtration. An analytical sample was prepared by recrystallization from methanol; M.P. 102°–5°, yield: 3.35 g. (82.6%). The IR and NMR spectra were consistent with the structure.

Anal. calc'd. for $C_{19}H_{20}F_3NO_3$ (percent): C, 62.12; H, 5.49; N, 3.82. Found (percent): C, 62.07; H, 5.38; N, 3.73.

EXAMPLE 17

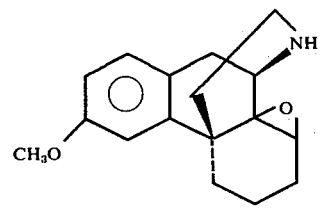

8,14-epoxy-3-methoxymorphinan (XX)

A mixture of 1.0 g. (2.72 mmole) of the epoxide XIg and 0.103 g. (2.72 mmole) of sodium borohydride in 5 ml. of absolute ethanol was refluxed during 5 minutes. After cooling, the reaction mixture was acidified with dilute hydrochloric acid and then extracted with ether. The aqueous layer was separated and make alkaline by the addition of aqueous ammonia and then extracted with methylene chloride. The resulting extracts were dried over $Na_2SO_4$ and concentrated in vacuo, to yield 800 mg. of an oil (XX) which was not further purified but used directly in the next transformation. The IR and NMR spectra were consistent with the structure.

EXAMPLE 18

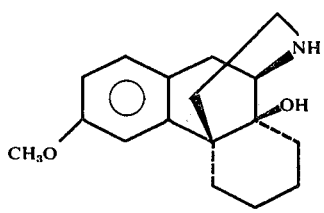

14-hydroxy-3-methoxymorphinan (XXI)

A solution of 800 mg. of the amine-epoxide (XX) in 10 ml. of tetrahydrofuran was added dropwise at room temperature, to a suspension of 50 mg. of lithium aluminum hydride in 5 ml. of dry tetrahydrofuran. After the addition had been completed, the reaction mixture was stirred and refluxed during fifteen minutes. Work up as usual yielded 700 mg. of an oil which was dissolved in ether and the resulting solution was filtered through a celitecharcoal mixture. The filtrate was treated with a saturated solution of hydrochloric acid in ether to yield 720 mg. of a white hydrochloride salt which after recrystallization from methanol melted at 243°–44° C.(dec.). The IR and NMR were consistent with the structure.

Anal. calc'd. for $C_{15}H_{23}NO_2 \cdot HCl \cdot \frac{1}{2}CH_3OH$ (percent): S, 64.50; H, 8.04; N, 4.30. Found (percent): C, 64.18; H, 7.81; N, 4.25.

EXAMPLE 19

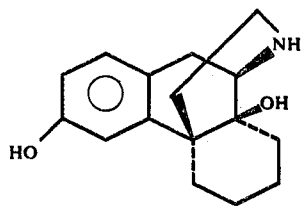

3,14-dihydroxymorphinan.(XXII)

A mixture of 140 mg. (0.5 mmole) of XXI and 0.55 g. of pyridine hydrochloride was heated under $N_2$ at 185°–95° C. for 1 hour. The mixture was cooled, treated with water and $NH_4OH$ and extract-d with $CHCl_3$. The $CHCl_3$ extracts were dried and evaporated to give a solid 53.6 mg. This was treated with ether and filtered. The solid was recrystallized from MeOH to give 50 mg./M.P. 264°–66° C. (d). The IR and NMR spectra were consistent with the structure.

Anal. calc'd. for $C_{19}H_{21}NO_2$ (percent): C, 74.1; H, 8.16; N, 5.40. Found (percent): C, 73.84; H, 8.35; N, 5.33.

EXAMPLE 20

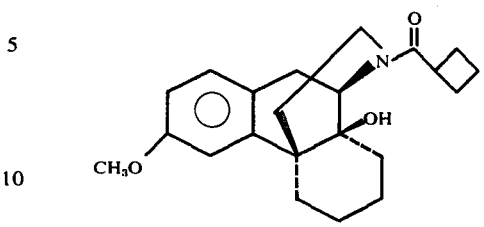

N-cyclobutylcarbonyl-14-hydroxy-3-methoxymorphinan (XXIII)

To a stirred and cooled solution of 400 mg. (0.00146 mole) of the amino alcohol XXI in 0.16 g. (0.002 mole) of dry pyridine and 5 ml. of methylene chloride, there was added, dropwise, a solution of 0.19 g. (0.0016 mole) of the acid chloride of cyclobutylcarboxylic acid in 5 ml. of methylene chloride. After stirring for ten minutes, the reaction mixture was washed successively with cold dilute aqueous hydrochlorid acid, dilute aqueous sodium hydroxide, water and finally with a saturated aqueous sodium chloride solution. After drying over $Na_2SO_4$ and evaporation of the solvent, there was obtained 400 mg. of an oil which crystallized on standing. The oil was treated with a small amount of cold ether and filtered to yield 320 mg. (61.6%) of crystals which after recrystallization from methanol melted at 183°–85° C. The IR and NMR spectra were consistent with the structure.

Anal. calc'd. for $C_{22}H_{29}NO_3$ (percent): C, 74.33; H, 8.22; N, 3.94. Found (percent): C, 74.19; H, 8.40; N, 3.75.

EXAMPLE 21

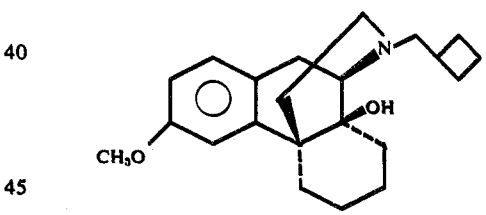

N-cyclobutylmethyl-14-hydroxy-3-methoxymorphinan (XIIb)

To a suspension of 1.0 g. of lithium aluminum hydride in 5 ml. of dry tetrahydrofuran was added at room temperature, under an atmosphere of nitrogen, a solution of 2.14 g. (6 mmole) of the amide XXIII in 25 ml. of tetrahydrofuran. The reaction mixture was then refluxed during thirty minutes and worked up as usual to yield 2.0 g. of an oil which was dissolved in ether and the resulting solution filtered through a celite-charcoal mixture.

Treatment with dry HCl gas yielded 2.04 g. of the hydrochloride; M.P. 235°–37° C. (dec.). Recrystallization from methanol increased the melting point to 248°–50° C. (dec.). The IR and NMR spectra were consistent with the structure.

Anal. calc'd. for $C_{22}H_{31}NO_2 \cdot HCl \cdot \frac{1}{2}H_2O$ (percent): C, 68.28; H, 8.60; N, 3.62. Found (percent): C, 68.25; H, 8.40; N, 3.75.

EXAMPLE 22

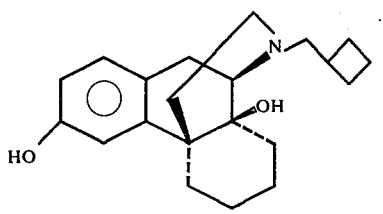

N-cyclobutylmethyl-3,14-dihydroxymorphinan (XIIIb)

A mixture of 1.0 g. (2.58 mmole) of XIIb and 10 ml. of 48% HBr was refluxed, under a nitrogen atmosphere, during the five minutes. After cooling, the reaction mixture was diluted with water and made basic with aqueous ammonium hydroxide. The aqueous basic mixture was extracted with chloroform and the combined chloroform extracts were dried over anhydrous sodium sulfate. After evaporation of the solvent, the residual oil (730 mg.) was taken up in dry ether and the resulting solution filtered through celite-charcoal. The filtrate was treated with a saturated solution of hydrogen chloride in dry ether. The hydrochloride salt thus obtained was collected by filtration and recrystallized from a methanol-acetone mixture to yield 565 mg. (56.5%) of crystals melting at 272°–74° C. (dec.). The IR and NMR spectra were consistent with the structure.

Anal. calc'd. for $C_{21}H_{29}NO_2.HCl.½CH_2OH$ (percent): C, 68.10; H, 8.14; N, 3.80.

EXAMPLE 23

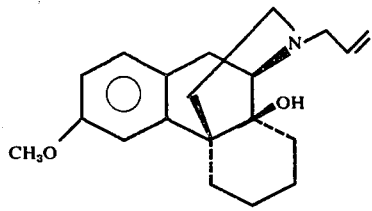

N-allyl-14-hydroxy-3-methoxymorphinan (XIIc)

To a stirred mixture of 900 mg. (3.3. mmole) of the aminoalcohol XXI and 1.7 g. (16.5 mmole) of triethylamine in 12 ml. of absolute ethanol was added, at room temperature and under nitrogen, a solution of 0.605 g. (5 mmole) of allyl bromide. After the addition had been completed, the reaction mixture was refluxed for eighteen hours and then evaporated to dryness. The residue was mixed with a 20% aqueous sodium carbonate solution and the resulting mixture extracted with several portions of ether. The combined ether extracts were dried over $Na_2SO_4$ and evaporated to yield 940 mg. of an oil which was dissolved in ether. The resulting solution was filtered through a celite-charcoal mixture and the filtrate concentrated at reduced pressure. The remaining oil was converted, in ether, into the hydrochloride salt. Recrystallization from a methanol-ether mixture yielded 600 mg. of a white solid melting at 244°–46° C. (dec.). Yield, 51.9%. The IR and NMR spectra were consistent with the structure.

Anal. Calc'd. for $C_{20}H_{27}NO_2.HCl$ (percent): C, 68.65; H, 8.07; N, 4.00. Found (percent): C, 68.01; H, 7.97; N, 3.90.

EXAMPLE 24

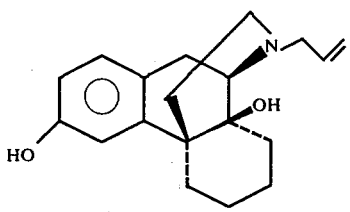

N-allyl-3,14-dihydroxymorphinan (XIIIc)

To a solution of 3.814 g. (12.135 mmole) of XIIc in 90 ml. of dry $CH_2Cl_2$ at −80° C. was added under $N_2$ dropwise a solution of 9.4252 g. (37.42 mmole) of $BBr_3$ of 20 ml. of dry $CH_2Cl_2$. The resulting reaction mixture was allowed to warm up to room temperature slowly for 18 hours. It was decomposed with ice water and the layers separated, the $CH_2Cl_2$ solution washed with water and saturated NaCl solution. It was dried and evaporated to give 3.76 g. of an oil. This was converted to its HCl salt in acetone. The HCl salt obtained was recrystallized from water-acetone to give 1.15 g. of a white solid. The mother liquor was concentrated and converted to its free base. The free base was chromatographed on $Al_2O_3$ (Act. 4) and eluted with $CHCl_3$ to give a fraction (1.35 g.) which was converted to its HCl salt. The HCl salt was recrystallized from $H_2O$-acetone to give 950 mg. The IR and NMR were consistent with the structure. Total yield 2.0 g. (50%).

Anal. calc'd. for $C_{19}H_{25}NO_2.HCl.½CH_3OH$ (percent): C, 66.56; H, 8.02; N, 3.98. Found (percent): C, 66.65; H, 7.76; N, 3.88.

EXAMPLE 25

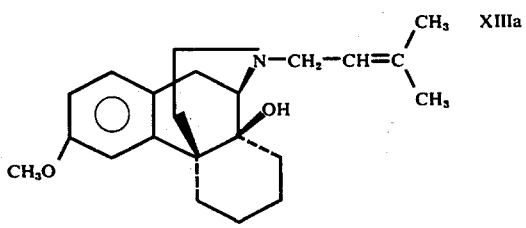

N-dimethylallyl-14-hydroxy-3-methoxymorphinan (XIId)

Substitution in the procedure of Example 23 for the allyl bromide used therein of an equimolar quantity of dimethylallyl bromide produces the title compound.

EXAMPLE 26

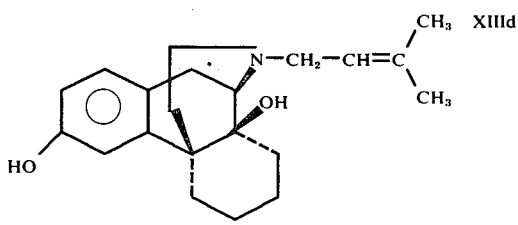

N-dimethylallyl-3,14-dehydroxymorphinan (XIIId)

Substitution in the procedure of Example 24 for the Compound XIIc used therein of an equimolar quantity of Compound XIIId produces the title compound.

EXAMPLE 27

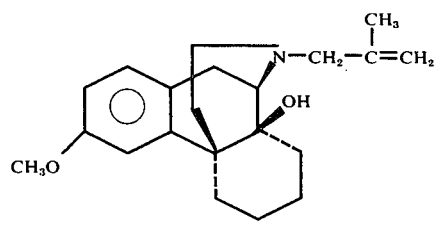

N-2'-methylallyl-4-hydroxy-3-methoxymorphinan (XIIe)

Substitution in the procedure of Example 23 for the allyl bromide used therein of an equimolar quantity of 2-methylallyl bromide produces the title compound.

EXAMPLE 28

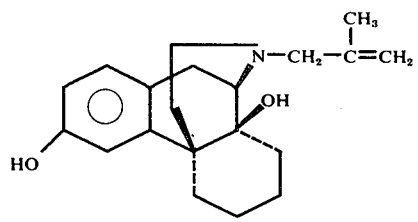

N-2'-methylallyl-3,14-dihydroxymorphinan (XIIIe)

Substitution in the procedure of Example 24 for the Compound XIIc used therein of an equimolar quantity of Compound XIIe produces the title compound.

EXAMPLE 29

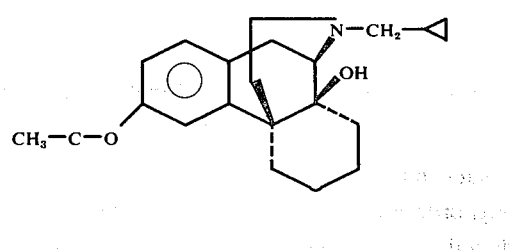

N-cyclopropylmethyl-3-acetoxy-14-hydroxymorphinan (XXXa)

Equimolar quantities of acetyl chloride, Compound XIIIa and pyridine are mixed together in dry methylene chloride and the resultant mixture is heated to 60° C. for several hours under a nitrogen atmosphere to produce the title compound.

EXAMPLE 30

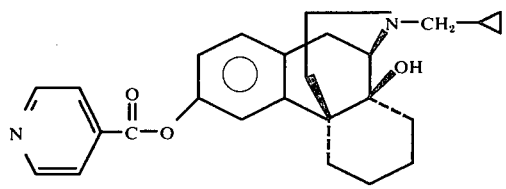

N-cyclopropylmethyl-3-nicotinoyloxy-14-hydroxymorphinan (XXXb)

Equimolar quantities of nicotinoyl chloride hydrochloride, Compound XIIIa and pyridine are mixed together in dry methylene chloride and the mixture is heated to 50° C. for 3 hours to produce the title compound.

EXAMPLE 31

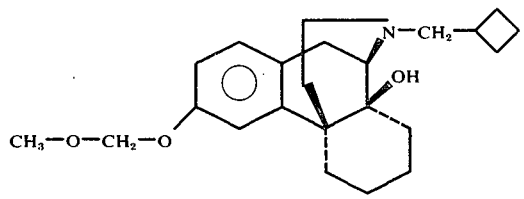

N-cyclobutylmethyl-14-hydroxy-3-methoxymethyloxomorphinan (XXXc)

One mole of compound XIIIb was placed in 3 liters of benzene. One mole of sodium methoxide was added, followed by the slow addition of 1 mole of chloromethyl ether with stirring. The solution was heated to reflux to yield the title product.

EXAMPLE 32

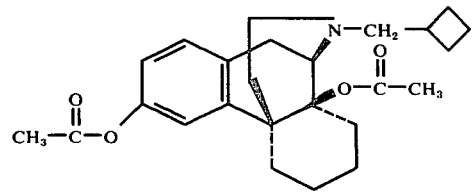

N-cyclobutylmethyl-3,14-diacetoxymorphinan (XXXd)

Two moles each of acetic anhydride and pyridine are mixed with one mole of Compound XIIIb in dry methylene chloride. The solution is heated to reflux for 24 hours under nitrogen to produce the title compound.

EXAMPLE 33

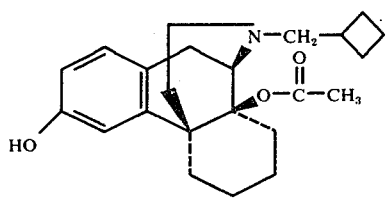

N-cyclobutylmethyl-14-acetoxy-3-hydroxymorphinan (XXXe)

One mole of Compound XXXd is dissolved in excess ethanol. One mole of sodium bicarbonate dissolved in water is added. If necessary, additional ethanol is added to maintain solution. The solution is allowed to stand at room temperature for several days. The solution is concentrated in vacuo at low temperature and then extracted with ether or methylene chloride. The aqueous phase is acidified and extracted with methylene chloride. The title product is isolated from the methylene chloride extract.

EXAMPLE 34

Resolution of dl-3,14-dihydroxy-N-cyclopropylmethylmorphinan into its d and l optical isomers (A) l-3,14-dihydroxy-N-cyclopropylmethylmorphinan dl-3,14-dihydroxy-N-cyclopropylmethylmorphinan (7.835 g., 35 mmole) as the free base was dissolved in 15 ml. of hot methanol. To this was added a solution of 3.75 g. (25 mmole) of l-tartaric acid in 15 ml. of hot methanol. The resulting solution was diluted with 30 ml. of acetone and let stand at 5° C. for 60 hours to crystallize. It was filtered to yield 3.2 g. of a crystalline solid (A). The mother liquor was evaporated to dryness and was made basic with aqueous ammonia to give approximately 5.0 g. of free base (B).

The solid (A) was recrystallized nine times from methanolacetone to give 500 mg. of the tartrate salt; $[\alpha]_D^{22} = -91.26$ (C., 0.4408; CHCl$_3$). This is l-isomer.

(B) d-3,14-dihydroxy-N-cyclopropylmethylmorphinan

The free base (B), 5.0 g., obtained in Step A above, was dissolved in hot methanol and an equivalent amount of d-tartaric acid dissolved in hot methanol was added. This yielded 5.0 g. of tartrate salt which was recrystallized seven times from methanolacetone; $[\alpha]_D^{22} = +63.679$ (C, 0.4028, MeOH).

The tartrate salt was liberated as its free base and recrystallized from CHCl$_3$; M.P. 178°–179° C.; weight 650 mg.; $[\alpha]_D^{22} = +91.83°$ C. (C, 0.4168, CHCl$_3$). This is the d-isomer.

EXAMPLE 35

Resolution of the Compounds of the instant invention into their respective optical isomers Substitution into the general procedure of example 34 for the dl-3,14-dihydroxy-N-cyclopropylmethylmorphinan used therein of an equimolar quantity of a dl-3,14-dihydroxy-N-substituted-morphinan will produce the resolved d and l isomers.

EXAMPLE 36

1-3,14-dihydroxy-N-cyclopropylmethylmorphinan pamoate 1-3,14-dihydroxy-N-cyclopropylmethylmorphinan (0.1 mole) is dissolved in hot methanol. A solution of 0.1 mole of pamoic acid dissolved in hot nitrobenzene is added to the first solution with vigorous agitation. The product that crystallizes is the pamoate salt.

EXAMPLE 37

Salt preparation of the compounds of the instant invention

Substitution in the procedure of Example 36 for the pamoic acid used therein of an equimolar quantity of sulfuric, nitric, phosphoric, phosphorous, hydrobromic, maleic, malic, ascorbic, citric, tartaric, lauric, stearic, palmitic, oleic, myristic, sulfuric, naphthalenesulfonic, linoleic or linolenic acid produces the corresponding acid addition salt of 1-3,14-dihydroxy-N-cyclopropylmethylmorphinan.

EXAMPLE 38

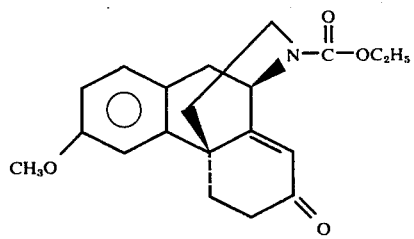

3-Methoxy-N-ethoxycarbonyl-7-Oxo-$\Delta^{8,14}$-morphinan (VIIIh)

Substitution in the procedure of Example 7 for the cyclopropanecarboxylic acid chloride used therein of an equimolar quantity of ethylchloroformate produces the title compound.

EXAMPLE 39

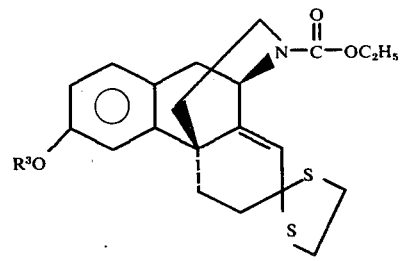

3-Methoxy-N-ethoxycarbonyl-7,7-ethylenedithio-$\Delta^{8,14}$-morphinan (IXh)

Substitution in the procedure of Example 8 for the Compound VIIIa used therein of an equimolar quantity of VIIIh produces the title compound IXh.

EXAMPLE 40

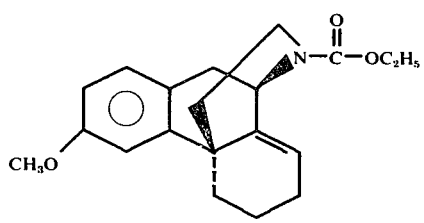

3-Methoxy-N-ethoxycarbonyl-$\Delta^{8,14}$-morphinan (X*h*)

Substitution in the procedure of Example 9 for the Compound IX*a* used therein of an equimolar quantity of IX*h* produces the title compound.

EXAMPLE 41

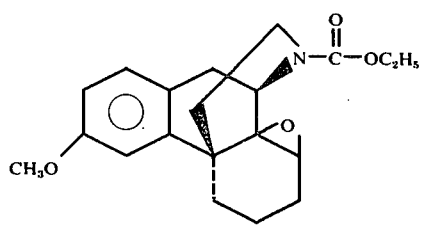

8,14-Epoxy-3-methoxy-N-ethoxycarbonylmorphinan (XI*h*)

To a stirred and cooled (5°–10° C) solution of compound X*h* (0.01 mole) in methylene chloride is added m-chloroperbenzoic acid (0.012 mole). The resulting solution is allowed to stand at room temperature for 5 hours. After filtration, the filtrate is washed with 10% sodium sulfate until a test for pexorides is negative (iodine-starch paper). The solution is washed with 5% sodium bicarbonate solution and dried over sodium sulfate. The mixture is filtered and the methylene chloride removed in vacuo to yield the desired title product XI*b*.

EXAMPLE 42

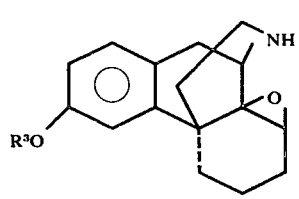

8,14-Epoxy-3-methoxymorphinan

A mixture of XI*h* (0.01 mole), 16 ml. of n-octanol and 28 g. of KOH pillets is refluxed under nitrogen for 45 minutes. After cooling, the mixture is treated with water and ether (60 ml.). The water layer is discarded and the organic layer extracted with 30 ml. of 2NHCl and 2 × 30 ml. of water. The combined aqueous extracts are basified with aqueous ammonia and the free base is taken up in ether, to yield the product after drying over sodium sulfate, filtration and evaporation.

We claim:

1. The process for the preparation of the compound having the formula

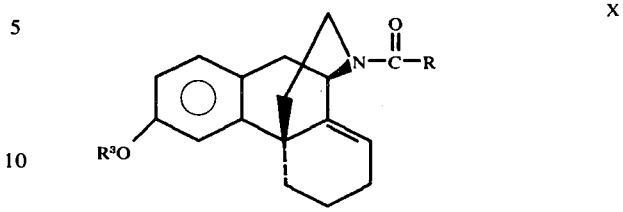

in which $R^3$ is (lower)alkyl and R is selected from the group consisting of

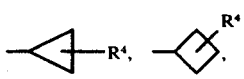

—$CF_3$ and $OR^1$ in which $R^1$ is (lower)alkyl and $R^4$ is H or $CH_3$; which process comprises the consecutive steps of A. treating the compound having the formula

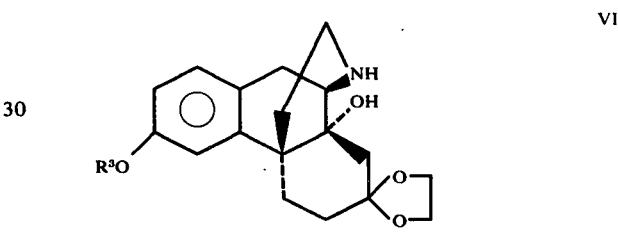

in which $R^3$ is (lower)alkyl with an acylating agent having the formula

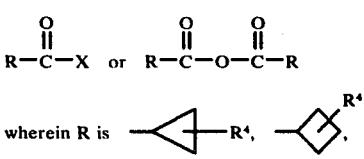

$CF_3$, or —$OR^1$ in which $R^1$ is (lower)alkyl, $R^4$ is H or $CH_3$, and X is chloro, bromo, iodo or a mixed anhydride moiety, in a molar ratio of about 1 to 2.0 moles of acylating agent per mole of Compound VI, in the presence of a tertiary amine to produce the compound having the formula

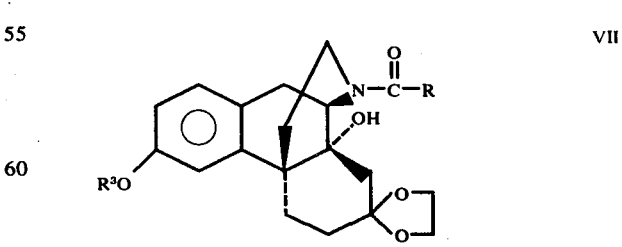

in which $R^3$ and R are as defined above;

B. heating Compound VII with sulfuric acid in a (lower)alkanol to produce the compound having the formula

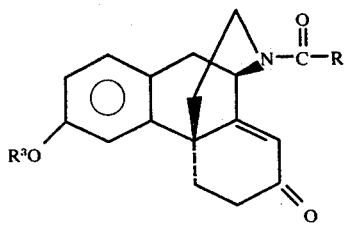

in which R³ and R are as above;

C. treating Compound VIII with excess ethanedithiol and boron trifluoride etherate in acetic acid to produce the compound having the formula

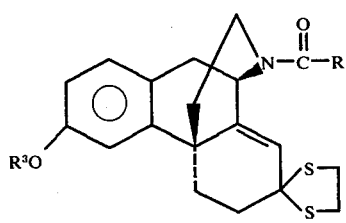

in which R³ and R are as above; and

D. heating Compound IX with Raney nickel in a (lower)alkanol to produce Compound X.

2. A process of claim 1 for the preparation of Compound X wherein R³ is (lower)alkyl and R is selected from the group consisting of

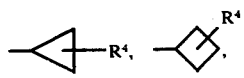

—$CF_3$ and $OR^1$ in which $R^1$ is (lower)alkyl and $R^4$ is H or $CH_3$; which process comprises the consecutive steps of A. treating the compound having the formula

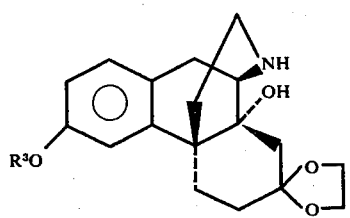

in which R³ is (lower)alkyl with an acylating agent having the formula

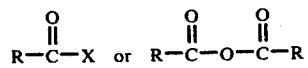

$CF_3$, or —$OR^1$ in which $R^1$ is (lower)alkyl, $R^4$ is H or $CH_3$ and X is chloro, bromo or iodo, in a ratio of about 1 to 1.3 moles of acylating agent per mole of Compound VI, in an inert organic solvent selected from the group consisting of benzene, toluene, xylene, methylene chloride, chloroform, ether, dioxane, tetrahydrofuran, in the presence of a tertiary amine selected from the group consisting of trimethylamine, triethylamine, pyridine, dimethylaniline, N-methylpyrrolidine, N,N-dimethylpiperidine and N-methylpiperidine in a molar ratio of 1 to 2 parts tertiary amine per mole of acylating agent to produce the compound having the formula

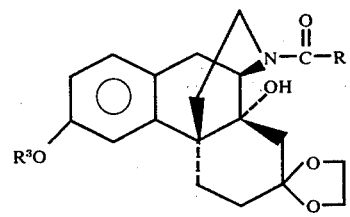

in which R³ and R are as defined above;

B. heating Compound VII with 0.3 to 0.7N sulfuric acid in a (lower)alkanol until dehydration occurs to produce the compound having the formula

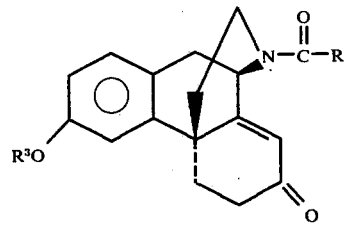

in which R³ and R are as above;

C. treating compound VIII with excess ethanedithiol and boron trifluoride etherate in acetic acid at room temperature for at least 3 hours to produce the compound having the formula

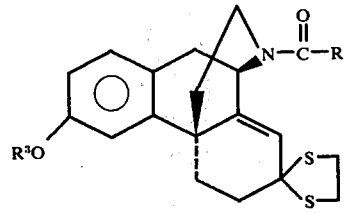

in which R³ and R are as above; and

D. heating Compound IX with Raney nickel in a (lower)alkanol to produce compound X.

3. The process of claim 1 for the preparation of the compound having the formula

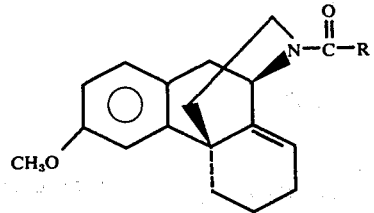

in which R is

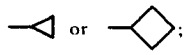

which process comprises the consecutive steps of
A. treating the compound having the formula

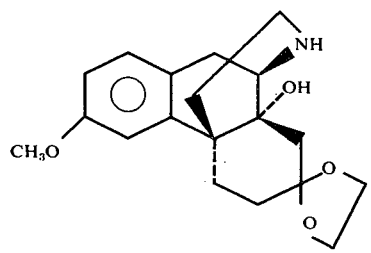
(VI)

with an acylating agent having the formula

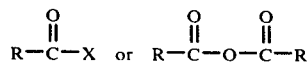

in which R is

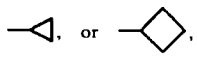

and X is chloro, bromo or iodo, in a ratio of about 1 to 1.2 moles of acylating agent per mole of Compound VI, in methylene chloride, in the presence of pyridine in a ratio of 1 to 2 moles of pyridine per mole of acylating agent, in a temperature range of about −10° C. to +40° C. to produce the compound having the formula

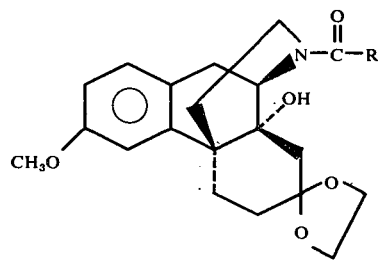
VII in which R is

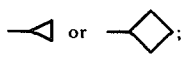

B. heating compound with about 0.5N sulfuric acid in methanol for about two to four hours to produce the compound having the formula

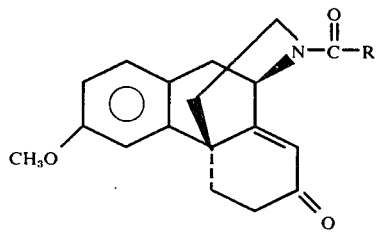
VIII in which R is

—◁ or —◇;

C. treating Compound VIII with excess ethanediol and boron trifluoride etherate in acetic acid at room temperature for at least three hours to produce the compound having the formula

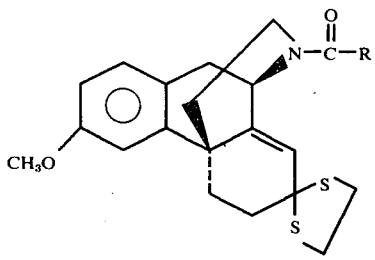
IX in which R is

—◁ or —◇;

and
D. refluxing Compound IX with Raney nickel in ethanol for about two hours to produce Compound X.
4. A compound having the formula

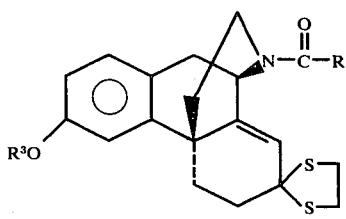
IX in which R is

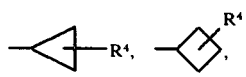

$CF_3$ or $-OR^1$ in which $R^1$ and $R^3$ are (lower)alkyl and $R^4$ is H or $CH_3$.
5. A compound of claim 4 wherein $R^3$ is methyl and R is cyclobutyl.
6. The compound of claim 4 wherein $R^3$ is methyl and R is cyclopropyl.
7. A compound having the formula

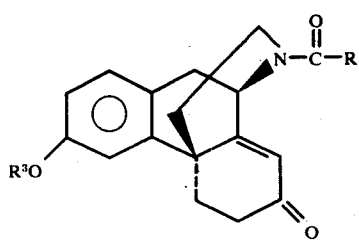
wherein R³ is (lower)alkyl and R is
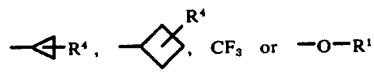
CF₃ or —O—R¹ in which R¹ and R³ are (lower)alkyl and R⁴ is H or CH₃.
8. A compound of claim 7 wherein R³ is methyl and R⁴ is H.
9. The compound of claim 7 wherein R³ is methyl and R is cyclobutyl.
10. The compound of claim 7 wherein R³ is methyl and R is cyclopropyl.
* * * * *

UNITED STATES PATENT AND TRADEMARK OFFICE
CERTIFICATE OF CORRECTION

PATENT NO. : 4,017,497
DATED : April 12, 1977
INVENTOR(S) : Gary Lim and John W. Hooper It is certified that error appears in the above–identified patent and that said Letters Patent are hereby corrected as shown below:

In Claim 7 (in first line of Column 42) delete "$CF_3$ or $-O-R^1$".

Signed and Sealed this twelfth Day of July 1977

[SEAL]

Attest:

RUTH C. MASON
*Attesting Officer*

C. MARSHALL DANN
*Commissioner of Patents and Trademarks*